United States Patent
Kurzbaum et al.

(10) Patent No.: US 12,172,916 B2
(45) Date of Patent: Dec. 24, 2024

(54) METHODS AND SYSTEMS FOR TREATING LIQUIDS INCLUDING CONTAMINANT MOLECULES

(71) Applicant: Bio Castle Water Technologies Ltd., Afula (IL)

(72) Inventors: Eyal Kurzbaum, Degania Alef (IL); Hadas Mamane, Caesarea (IL); Ofir Menashe, Shimshit (IL); Dror Avisar, Zoran (IL)

(73) Assignee: Bio Castle Water Technologies Ltd., Afula (IL)

( * ) Notice: Subject to any disclaimer, the term of this patent is extended or adjusted under 35 U.S.C. 154(b) by 1044 days.

(21) Appl. No.: 16/967,884

(22) PCT Filed: Feb. 7, 2019

(86) PCT No.: PCT/IB2019/050990
§ 371 (c)(1),
(2) Date: Aug. 6, 2020

(87) PCT Pub. No.: WO2019/155397
PCT Pub. Date: Aug. 15, 2019

(65) Prior Publication Data
US 2021/0047216 A1    Feb. 18, 2021

Related U.S. Application Data

(60) Provisional application No. 62/627,211, filed on Feb. 7, 2018.

(51) Int. Cl.
  C02F 1/34    (2023.01)
  C02F 1/32    (2023.01)
(Continued)

(52) U.S. Cl.
  CPC .............. *C02F 3/348* (2013.01); *C02F 1/325* (2013.01); *C02F 3/1284* (2013.01); *C02F 2101/305* (2013.01); *C02F 2305/06* (2013.01)

(58) Field of Classification Search
  CPC ...... C02F 3/34; C02F 1/32; C02F 3/12; C02F 1/72; C02F 1/70; C02F 1/36; C02F 1/30; B01D 32/34
  See application file for complete search history.

(56) References Cited

U.S. PATENT DOCUMENTS

2002/0195389 A1    12/2002    Perriello
2005/0119353 A1    6/2005     Detorres
(Continued)

FOREIGN PATENT DOCUMENTS

WO    2010122545 A1    10/2010
WO    2012160526 A3    11/2012

OTHER PUBLICATIONS

CN 107935272 A; A High-efficient Treatment Device For Photo-catalysis Sewage; Wang, Yong-sheng;Date Filed Dec. 25, 2017 (Year: 2018).*

*Primary Examiner* — Walter D. Griffin
*Assistant Examiner* — Cameron J Allen
(74) *Attorney, Agent, or Firm* — The Roy Gross Law Firm, LLC; Roy Gross

(57) ABSTRACT

The present invention provides systems and methods for treating liquids including contaminant molecules dispersed therein by combining physical treatment, biological treatment and/or chemical treatment.

10 Claims, 10 Drawing Sheets

(51) Int. Cl.
*C02F 3/12* (2023.01)
*C02F 3/34* (2023.01)
*C02F 101/30* (2006.01)

(56) References Cited

U.S. PATENT DOCUMENTS

2008/0138883 A1* 6/2008 Young .................. C12N 1/26
 435/262.5
2011/0089107 A1 4/2011 Marsolek et al.
2012/0247273 A1 10/2012 Fahs, II et al.

* cited by examiner

METHODS AND SYSTEMS FOR TREATING LIQUIDS INCLUDING CONTAMINANT MOLECULES

CROSS-REFERENCES TO RELATED APPLICATIONS

This application is related to and claims priority from commonly owned U.S. Provisional Patent Applications Ser. No. 62/627,211, entitled: Process to Dismantle Chemotherapy and Non-Biodegradable Micro/Nano Pollutants Using an Oxidative Bio-Reactor (OBR), filed on Feb. 7, 2018, the disclosure of which is incorporated by reference in its entirety herein.

TECHNICAL FIELD

The present invention relates to the field of water and wastewater treatment.

BACKGROUND OF THE INVENTION

The rising and expanding use of chemicals along with growing populations and increasing urbanization present new challenges to wastewater treatment, which are not met by conventional Wastewater Treatment Plants (WWTPs). Most WWTPs fail to provide an effective barrier to substances, such as pharmaceutical and personal care products, due to their specific metabolic properties and resistance to physico-chemical treatments. Some of these substances are likely to result in chronic direct or indirect effects on public health and ecosystems. One such result is the feminization of fish due to endocrine-effect substances in the aquatic environment.

SUMMARY OF THE INVENTION

The present invention provides systems and methods for treating liquids including contaminant molecules dispersed therein by combining physical treatment, biological treatment and/or chemical treatment. The physical treatment includes using a ultraviolet source. The ultraviolet source emits light at a predetermined frequency and for a predetermined time such that the contaminant molecules absorb the UV light and become destabilized to a subsequent or predetermined energy level. At this subsequent or predetermined energy level, the contaminant molecules become biodegradable molecules. Contemporaneously or simultaneously to the physical treatment, a biological treatment takes place. The biological treatment includes exposing the bio-degradeable moles in the liquid to capsules, which are configured for digesting and/or neutralizing the biodegradable molecules. The capsules are operable at the subsequent or predetermined energy level of the biodegradable molecules (formerly, the contaminat molecules). At this subsequent energy level, the capsules treat the bio-degradable molecules, for example, by neutralizinig and/or digesting them. Contemporaneously or simultaneously to the physical and biological treatments, the chemical treatment may occurs. The chemical treatment includes reactive particles that are added in order to accelerate and/or catalyze the biodegradable molecules treatment.

Embodiments of the invent on are directed to a method for treating liquids including contaminant molecules dispersed therein. The method comprises: providing at least one capsule into a volume of liquid including contaminant molecules dispersed therein, the at least one capsule configured for treating biodegradable molecules at a predetermined energy level; exposing the liquid to ultraviolet (UV) light at a predetermined frequency for at least a predetermined time, such that the absorption of the UV light by the contaminant molecules destabilizes the contaminant molecules to at least the predetermined energy level, where the contaminant molecules become biodegradable molecules; and, treating the biodegradable molecules with the at least one capsule operable at the predetermined energy level.

Optionally, the method is such that, the treating includes digesting the biodegradable molecules by the at least one capsule.

Optionally, the method is such that, the digesting the biodegradable molecules results in one or more of: Carbon Dioxide, secondary metabolites and, cell proliferations.

Optionally, the method is such that, the treating includes neutralizing the biodegradable molecules by the at least one capsule.

Optionally, the method is such that, the treating the biodegradable molecules with the at least one capsule occurs while the liquid is exposed to the UV light.

Optionally, the method is such that, the treating the biodegradable molecules with the at least one capsule occurs simultaneously with the liquid being exposed to the UV light.

Optionally, the method is such that, the at least one capsule includes a plurality of capsules.

Optionally, the method is such that, the contaminant molecules are at lest one of: treatment resistant molecules, and semi-resistant molecules.

Optionally, the method is such that, the contaminant molecules include at least one of: antibiotic, antifungi, Chemotheraphy drugs, Anti inflamatory drugs, Antituberculosis agents, antiviral agents, Antineoplastics, Cardiovascular agents, Anti iflamatory agents, Anticholinergic chronotropic agents, Antihypertensive combinations, Beta-adrenergic blocking agents, calcium channel blocking agents, catecholamines, diuretics, inotropic agents, miscellaneous cardiovascular agents, peripheral vasodilators, renin inhibitors, sclerosing agents, vasodilators, vasopressin antagonists, vasopressors, central nervous system agents, anorexiants, anticonvulsants, antiemetic/antivertigo agents, antiparkinson agents, anxiolytics, sedatives, and hypnotics, cholinergic agonists, cholinesterase inhibitors, Central Nervous System (CNS) stimulants, drugs used in alcohol dependence, general anesthetics, miscellaneous central nervous system agents, muscle relaxants, coagulation modifiers, antiplatelet agents, heparin antagonists, miscellaneous coagulation modifiers, platelet-stimulating agents, thrombolytics, gastrointestinal agents, genitourinary tract agents, immunologic agents, metabolic agents, miscellaneous agents, nutritional products, plasma expanders, psychotherapeutic agents, respiratory agents, radiologic agents, topical agents, diamine, polyamine, peptids, glycolpeptide, lipopeptide, phenols, polyphenols, hormone and steroid.

Optionally, the method is such that, the ultraviolet light is at least one of: polychromatic light, monochromatic light, high pressure light, medium pressure light, low pressure light, light emitting diodes and a combination thereof.

Optionally, the method is such that, the volume of the liquid is provided into a container.

Optionally, the method is such that, the liquid includes water.

Optionally, the method is such that, the water includes wastewater.

Optionally, the method is such that, the wastewater is at least one of sewage or sanitary effluents.

Optionally, the method is such that, the wastewater includes industrial wastewater.

Optionally, the method is such that, the at least one capsule and ultraviolet light operate contemporaneously.

Optionally, the method is such that, the at least one capsule and the ultraviolet light operate simultaneously.

Optionally, the method is such that, the each capsule comprises: a solid matrix of nutrients comprising one or more of: carbon source, water, NaCl, iron, magnesium, nitrogen, phosphorus, sulfurmicro-nutrients and degradation enzymes.

Optionally, the method is such that, the treating the biodegradable molecules includes adding reactive particles to the liquid to accelerate the biodegradable molecules digestion.

Optionally, the method is such that, the treating the biodegradable molecules includes adding nano particles to the liquid to accelerate the biodegradable molecules digestion.

Optionally, the method is such that, each capsule comprises: at least one inner core including a solid matrix of nutrients for microorganism growth; an inner membrane surrounding said at least one inner core, said at least one inner core includes a population of microorganisms; and, an outer porous membrane surrounding said inner membrane.

Optionally, the method is such that, the microorganisms include dried microorganisms.

Optionally, the method is such that, the outer porous membrane is insoluble in water.

Optionally, the method is such that it additionally comprises adding free radicals into the volume of the liquid.

Optionally, the method is such that, the treating the biodegradable molecules includes facilitating contact between each capsule and the biodegradable molecules.

Optionally, the method is such that, the facilitating contact includes at least one of stirring the liquid or or creating turbulence in the liquid.

Optionally, the method is such that, the UV light creates radiation to induce at least one of a photo-catalysis or photolysis effect or an oxidative reaction, in the biodegradable molecules.

Embodiments of the invention are directed to a system for treating liquids including contaminant molecules dispersed therein. The system comprises: a container for holding a volume of liquid, the volume of liquid including contaminant molecules dispersed therein; at least one capsule operative in the volume of liquid held in the container, the at least one capsule configured for treating biodegradable molecules at a predetermined energy level; and, a ultraviolet (UV) light source configured for emitting UV light into the volume of liquid in the container, the UV light at a predetermined frequency for at least a predetermined time, such that the absorption of the UV light by contaminant molecules in the volume of liquid destabilizes the contaminant molecules to at least the predetermined energy level, where the contaminant molecules become biodegradable molecules.

Optionally, the system is such that, the at least one capsule includes a plurality of capsules.

Optionally, the system is such that, the UV light source extends at least partially into the chamber.

Optionally, the system is such that, the container is configured for creating a flow path for the liquid therein.

Optionally, the system is such that, the container includes a liquid inlet and a liquid outlet.

Optionally, the system is such it additionally comprises a stirrer in communication with the container, for creating the flow path for the liquid in the container.

Optionally, the system is such that it additionally comprises a mechanism for introducing air into the container, for creating turbulence in the liquid in the container.

Optionally, the system is such that, each capsule comprises: at least one inner core including a solid matrix of nutrients for microorganism growth; an inner membrane surrounding said at least one inner core, said at least one inner core includes a population of microorganisms; and, an outer porous membrane surrounding said inner membrane.

Optionally, the system is such that, the microorganisms are selected for water decontamination.

Optionally, the system is such that, the solid matrix of nutrients comprises one or more of: carbon source, water, NaCl, iron, magnesium, nitrogen, phosphorus, sulfur, micro-nutrients and degradation enzymes.

Optionally, the system is such that, the microorganisms include dried microorganisms.

Optionally, the system is such that, the outer porous membrane is insoluble in water.

Optionally, the system is such that, the microorganisms comprise a homogenous population of microorganisms.

Optionally, the system is such that, the microorganisms comprise a heterogeneous population of microorganisms.

Optionally, the system is such that, the solid matrix of nutrients comprises an agar.

Optionally, the system is such that, the inner core is coated with a controlled release polymer.

Optionally, the system is such that, at least one of the inner membrane or the inner core further comprises an enzyme.

Optionally, the system is such that, the inner core further comprises an agent selected from the group consisting of an amino acid, an enzyme, a sugar, an iron, a salt and an essential element.

Optionally, the system is such that, each capsule is capable of supporting biofilm formation within.

Optionally, the system is such that, the inner membrane further comprises additional elements which support biofilm formation thereon.

Optionally, the system is such that, the additional elements comprise glass beads.

Optionally, the system is such that, the inner membrane further comprises activated carbon granules or activated carbon chips.

Optionally, the system is such that, the outer porous membrane is fabricated from a polymer selected from at least one of: PVAL (polyvinyl-alcohol), Polyethersulfone (PES), Cellulose Acetate, Cellulose Nitrate, Ethyl Cellulose, Nitrocellulose Mixed Esters, Polycarbonate film, Nylon, PVDF (poly(vinylidene fluoride)) and Polysulfone.

Optionally, the system is such that, the outer porous membrane is fabricated from a polymer comprising Cellulose Acetate.

Optionally, the system is such that, the outer porous membrane is fabricated from a polymer comprising Ethyl Cellulose.

Optionally, the system is such that, the outer porous membrane is resistant to biofilm formation.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings.

DESCRIPTION OF THE PREFERRED EMBODIMENTS

Figure 1:
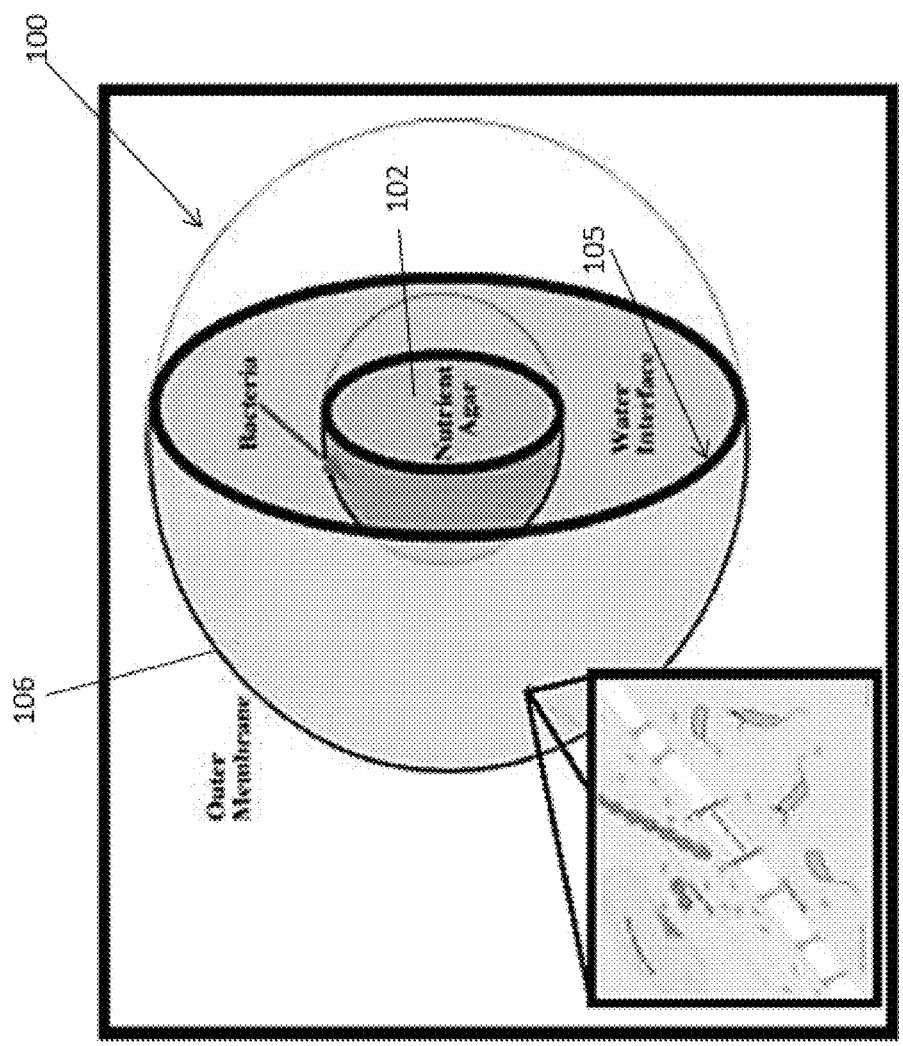
FIG. 1 is an illustration of an SBP capsule according to an embodiment of the present invention.

The present invention is not limited in its application to the details of construction and the arrangement of the components set forth in the following description. The invention is capable of other embodiments, or of being practiced or carried out in various ways. Also, it is to be understood that the phraseology and terminology employed herein is for the purpose of description and should not be regarded as limiting.

The present invention provides an apparatus and method for decontaminating fluids, typically liquids, but may also include gases and combinations of liquids and gases. The liquids include, for example, water, such as wastewater, industrial wastewater, sewage, sanitary effluents and the like from contaminated water, for example, with recalcitrant contaminants that resist conventional biological, chemical and physical treatments. The present invention involves combining biological, physical and/or chemical treatments contemporaneously or simultaneously in order to efficiently decontaminate wastewater, by neutralizing and digesting the contaminants therein.

The present invention provides an apparatus for decontaminating liquids by digesting or otherwise neutralizing contaminant molecules. Contaminant molecules include molecules having, for example double bonds, benzene rings and the like, which require investments of high energy in order to destabilize and/or break these double bonds, and other high energy bonds. With these bonds destabilized and/or broken, the molecules are at energy levels in which small bioreactor platform (SBP) capsules can operate on the molecules and treat them, for example, by digesting the molecules. Contaminant molecules are, for example, treatment resistant molecules, semi-resistant molecules, antibiotic, antifungi, Chemotherapy drugs, Anti-inflammatory drugs, Antituberculosis agents, antiviral agents, Antineoplastic, Cardiovascular agents, Anti-inflammatory agents, Anticholinergic chronotropic agents, Antihypertensive combinations, Beta-adrenergic blocking agents, calcium channel blocking agents, catecholamines, diuretics, inotropic agents, miscellaneous cardiovascular agents, peripheral vasodilators, renin inhibitors, sclerosing agents, vasodilators, vasopressin antagonists, vasopressors, central nervous system agents, anorexiants, anticonvulsants, antiemetic/antivertigo agents, antiparkinson agents, anxiolytics, sedatives, and hypnotics, cholinergic agonists, cholinesterase inhibitors, Central Nervous System (CNS) stimulants, drugs used in alcohol dependence, general anesthetics, miscellaneous central nervous system agents, muscle relaxants, coagulation modifiers, antiplatelet agents, heparin antagonists, miscellaneous coagulation modifiers, platelet-stimulating agents, thrombolytic, gastrointestinal agents, genitourinary tract agents, immunologic agents, metabolic agents, miscellaneous agents, nutritional products, plasma expanders, psychotherapeutic agents, respiratory agents, radiologic agents, topical agents, diamine, polyamine, peptides, glycolpeptide, lipopeptide, phenols, polyphenols, hormone, steroid and the like.

The present invention involves treating liquids, such as water and wastewater, by combined treatment of physico-chemical treatment elements and biological paths (bio-chemicals).

The combined treatment includes achieving synergy between at least two treatment approaches, for example, light exposure (physical treatment) and biomass treatment (biological treatment). Other elements that can be incorporated into the combined treatment are, for example, free radicals, reactive particles, nano particles and the like (chemical treatment).

The light exposure includes ultraviolet (UV) radiation, emitted at a frequency and length of time sufficient to be absorbed by the contaminant molecules so as to render the contaminant molecules biodegradable, and as a result, these biodegradable molecules are of an increased sensitivity and are accessible to bio-chemical activity by the biomass located within the designated capsules. With the contaminant molecules becoming biodegradable, the biomass within the designated capsules can operate on the molecules, neutralizing and/or digesting them. The digestion process of the biodegradable molecules may result in one or more of: Carbon Dioxide, secondary metabolites and, cell proliferations.

The combined physico-chemical and biological treatment present unique advantages in relation to increasing contaminants treatment yield and kinetics. This treatment involves conducting the combined treatments at the same space and time, which was previously considered impossible due to the lethal effect of the physico-chemical (UV light exposure) treatment on biomass (biological treatment). The present invention capability to combine these treatments allows treating molecules that were previously considered as treatment resistant or hard to treat molecules.

The present invention provides treatment solutions for various industries, including: pharmaceuticals, hospitals, sanitary waste and the like.

The present invention can save treating infrastructure: reducing the need for an additional reactor or chamber and other associated infrastructure that are required for the separation of the biological treatment from the physic-chemical treatment. In addition, the present invention can also reduce energy consumption and costs such as: water cycling, time reducing for UV operation and the like.

The present invention utilizes the Small Bioreactor Platform (SBP) technology as disclosed in U.S. Pat. No. 8,673,606, entitled: Microorganism Comprising Particles and Uses of Same, and WO 2010/122545 A9 (from PCT Application No. PCT/IL2010/000256, entitled: Microorganism Comprising Particles and Uses of Same), both of these documents incorporated by reference herein in their entirety. The SBP capsules encase specific microorganism cultures, selected for water decontamination, for the biodegradation of various contaminants. The SBP capsules are coated with, for example, a semi-permeable membrane (micro-filtration membrane) which only allows dissolved molecules and compounds to penetrate across the membrane while keeping the microorganisms inside in favorable micro-cosmos conditions. The physical barrier provides bacterial culture protection and prevents negative interactions with wastewater microorganisms (i.e., protozoa, bacteria), as well as, from other external hazards such as UV radiation and free radicals.

FIG. 1 is an illustration of an SBP capsule 100. The capsule 100 physically separates the introduced microbial culture inside the capsule from the outer natural microbial flora of the wastewater, while enabling the trafficking of dissolved molecules through the capsule membrane. The SBP capsule 100 includes an inner core 102 including a solid matrix of nutrients for microorganism growth, an inner membrane 105 surrounding the inner core 102 and a population of microorganisms, for example, homogenous, heterogeneous or dried microorganisms and an outer porous membrane 106 surrounding the inner membrane 105.

The solid matrix of the inner core 102, for example, includes nutrients, such as nutrients which support microorganism growth and/or which augment the microorganism activity (e.g., decontaminating activity). The inner core 102 may include, for example, an agar, and agents, such as a source of amino acids and nitrogen (e.g., beef, yeast extract, tryptone), a sugar or carbon source (e.g., glucose), water, various salts (e.g., Sodium Chloride (NaCl)), essential elements (e.g., iron, magnesium, nitrogen, phosphorus, sulfur, sulfurmicro-nutrients, and other micro-nutrients), other compounds (e.g., lactate), enzymes (e.g., degradation enzymes) and the like. The inner core 102 may further be coated with a controlled release polymer.

The inner membrane 105, for example, may include an enzyme, activated granules, activated carbon chips or additional elements, such as glass beads, which support biofilm formation. Once the SBP capsule 100 is activated, the inner membrane 105 is removed.

The outer membrane 106 is, for example, porous and insoluble in water (water insoluble). The outer membrane 106 is resistant to biofilm formation. The outer membrane 106 is, for example, fabricated from a polymer selected from at least one of: PVAL (polyvinyl-alcohol), Polyethersulfone (PES), Cellulose Acetate, Cellulose Nitrate, Ethyl Cellulose, Nitrocellulose Mixed Esters, Polycarbonate film, Nylon, PVDF (poly(vinylidene fluoride)) and Polysulfone.

The SBP capsule 100 is, for example, approximately 2.5 cm long and 0.8 cm in diameter and is capable of supporting biofilm formation within.

Figure 2:
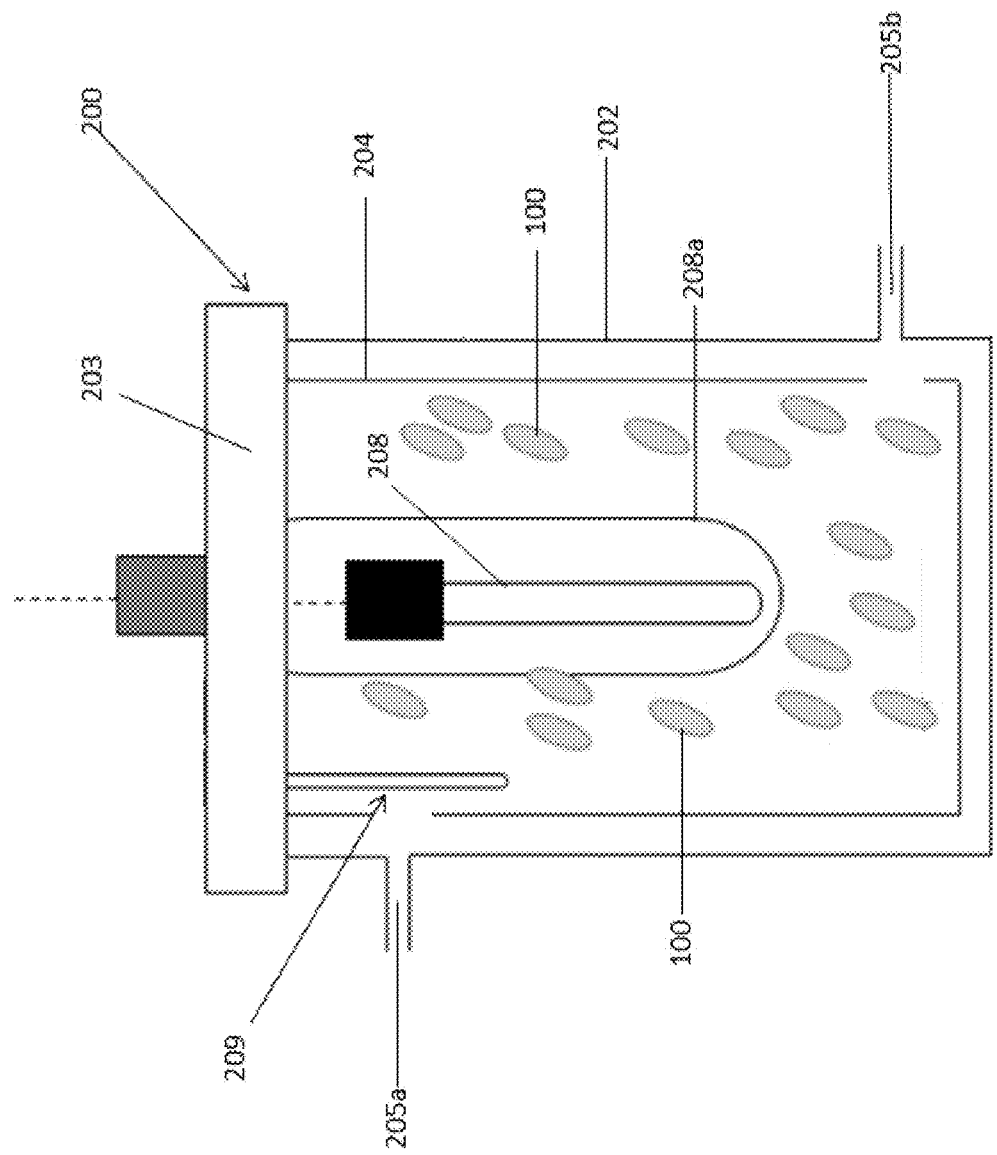
FIG. 2 is a cross-section view of the apparatus according to an embodiment of the present invention.

FIG. 2 is a cross-section view of the apparatus 200 or system, known, as an oxidative bio-reactor (OBR), for treating liquids such as wastewater. The apparatus 200 includes a container 202 with a cover 203, and an interior or chamber 204. The container 202 includes an inlet 205a and an outlet 205b. A fluid flow pathway or circulation pathway is created in the chamber as wastewater flows from the inlet 205a to the outlet 205b. The inlet 205a and outlet 205b are connected to pipes or tubes that carry the wastewater.

An ultraviolet (UV) radiation source 208 extends at least partially from the cover 203 into the chamber 204. The UV radiation source 208 is protected by a sleeve 208a, which encloses the UV radiation source 208, The UV radiation source 208 is, for example, adjustable, allowing for the emission of multiple wavelengths of UV light, including, for example, polychromatic light, or a light of a specific wavelength, for example, by monochromatic light. The UV source 208 may also be one of high, medium or low pressure light, light emitting diodes and the like. The UV source 208 can be activated manually or controlled by a computerized controller (not shown), over wired and/or wireless networks, or combinations thereof.

The UV source 208 may also be activated for a predetermined time, for example, approximately 48 hours, at a predetermined time intervals (for example, by a processor based controller or other timing device) on demand. Apparatus 200 may further include a port 209 for adding reactive particles, such as $H_2O_2$ and $O_3$, nano particles, selective catalysts (i.e., $TiO_2$) and the like, which are added into the liquid (e.g., wastewater) in order to increase the treatment efficacy and rate by improving and accelerating the biodegradable molecules digestion. The free radicals can accelerate the digestion of the contaminants.

The contaminants treatable by the disclosed apparatus 200 and system include, for example, treatment resistant molecules, semi-resistant molecules, antibiotic, antifungi, Chemotherapy drugs, Anti-inflammatory drugs, Antituberculosis agents, antiviral agents, Antineoplastic, Cardiovascular agents, Anti-inflammatory agents, Anticholinergic chronotropic agents, Antihypertensive combinations, Beta-adrenergic blocking agents, calcium channel blocking agents, catecholamines, diuretics, inotropic agents, miscellaneous cardiovascular agents, peripheral vasodilators, renin inhibitors, sclerosing agents, vasodilators, vasopressin antagonists, vasopressors, central nervous system agents, anorexiants, anticonvulsants, antiemetic/antivertigo agents, antiparkinson agents, anxiolytics, sedatives, and hypnotics, cholinergic agonists, cholinesterase inhibitors, CNS stimulants, drugs used in alcohol dependence, general anesthetics, miscellaneous central nervous system agents, muscle relaxants, coagulation modifiers, antiplatelet agents, heparin antagonists, miscellaneous coagulation modifiers, platelet-stimulating agents, thrombolytic, gastrointestinal agents, genitourinary tract agents, immunologic agents, metabolic agents, miscellaneous agents, nutritional products, plasma expanders, psychotherapeutic agents, respiratory agents, radiologic agents, topical agents, diamine, polyamine, peptides, glycolpeptide, lipopeptide, phenols, polyphenols, hormone, steroid and the like.

The chamber 204 accommodates operative SBP capsules 100 which float or are otherwise dispersed in the chamber by the wastewater. The SBP capsules 100, for example, travel or circulate in the chamber in accordance with the fluid flow pathway.

The apparatus 200 may also include stirrers, mixers, air diffusers, blower, bubblers in order to maintain or augment the circulation flow path, and also oxygenate and/or create turbulence in the water/wastewater/liquid, to prevent stagnation and additional contaminant build-up. Additionally, for example, warm water jackets, sensor ports, and the like, may be employed with the apparatus 200.

In operation, for example, liquid, e.g., wastewater enters the interior 204 through the inlet 205a, and flows in accordance with a flow or circulation path toward the outlet 205b. The wastewater flow circulates the operative SBP capsules 100, along a circular path in the interior 204 in order to facilitate contact between each SBP capsule and the biodegradable molecules. The SBP capsules can be further circulated using mechanism for introducing air into the container 202, for example, vortex and/or air diffusers. This mechanism configured for stirring the liquid and creating turbulence in the liquid. At a predetermined time intervals or on demand, the UV radiation source 208 emits light at a desired wavelength and intensity. This UV light emission is absorbed by the contaminant molecules such that the contaminant molecules become biodegradable and temporarily destabilized via direct photolysis, photo-catalysis, oxidative reaction and the like. This momentary unstable state is short, e.g., on the order of milliseconds to seconds. During this unstable state, the bonds between the now biodegradable molecules disassemble, lowering the energy to the level of energy required for digesting and neutralizing the biodegradable molecules, by the capsules 100. As the contaminant molecules have become biodegradable molecules, they are at an energy level where the capsules 100 can now operate on the biodegradable molecules to further destabilize and/or break the bonds, causing digestion and/or neutralization of the biodegradable molecules. Some digestion products include one or more of carbon dioxide, secondary metabolites and cell proliferations. Additionally, during this process, the emitted UV light causes DNA damage to pathogens located within the liquid, which accelerates cell lysis while not affecting the biomass within the SBP capsules 100.

Contemporaneously or simultaneously to the exposure of the liquid to UV light, the biodegradable molecules are met with viable bacteria or enzymes located within the SBP capsules 100 which in turn digest or neutralize the biodegradable molecules. This reaction occurs on the surface of the SBP capsules 100. The SBP capsules 100 may also include Nano-materials (NMs) integrated and embedded within the outer membrane 106 of the SBP capsules. These NMs are able to simultaneously accelerate the photocatalytic degradation of contaminants and allow the biological process to digest the biodegradable compounds to photocatalytically transformed molecules or even to their mineral forms. These reactions can create free radicals, such as $H_2O_2$, that in combination with UV radiation can be converted into OH radical, which is a much more reactive radical. The OH radical reacts with contaminants on the surface of the SBP capsules 100 such that it further allows disintegrating treatment resistance molecules. A wide range of NMs can be exploited including, for example, graphene and its derivatives, graphitic carbon nitride (g-$C_3N_4$), polymeric nanocomposites, metal oxides (e.g., $TiO_2$ and $WO_3$ nanosheets), metallates (e.g., $Bi_2WO_4$ and $Bi_2MoO_6$), metal oxyhalides BiOBr and BiOI) and transition metal dichalcogenides.

The biomass located within SBP capsules 100 is also directed for reducing secondary metabolites that are formed by an oxidative action or mineralized by the bacterial activity during the biodegradation process of the treatment resistance molecules. This allows achieving safer effluents to, for example, drinking water treatment plants (DWTP), wastewater treatment plants (WWTP) and environmental discharging.

Increasing the biodegradation compliance and rate of treatment resistance molecules reduces the required hydraulic retention time, resulting a smaller treatment facility and significant reduction in CAPEX (capital expenses) and OPEX (operational expenses).

Figure 3:
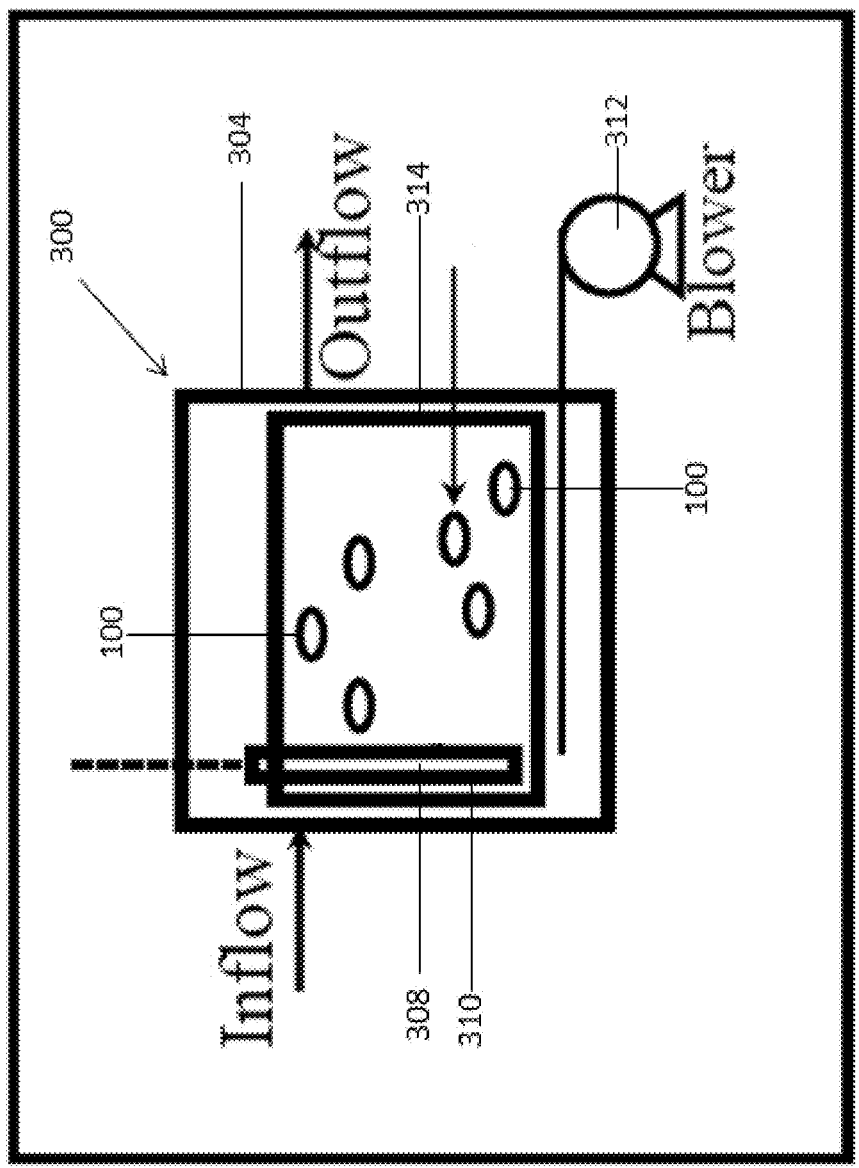
FIG. 3 is a cross-section view of the apparatus according to another embodiment of the present invention.

FIG. 3 is a cross-section view of another embodiment apparatus 300 for treating wastewater. The apparatus 300 is similar in construction and operation to apparatus 200, as detailed above, except where indicated. The apparatus 300 includes a body 304 defining a fluid flow path that extends from an inlet to an outlet. The inlet and outlet define a flow path of wastewater through the body 304. Body 304 includes a perforated cage or net 314 enclosing SBP capsules 100 and a vertically positioned UV radiation source 308 enclosed within a protective cover 310. Apparatus 300 further includes a blower or bubbler 312 which forces air into the interior (of the container or chamber) in order to create bubbles in the liquid. These bubbles supply dissolved oxygen to the wastewater and keep the water in a moving and/or turbulent state, to avoid stagnation of the liquid.

Figure 4:
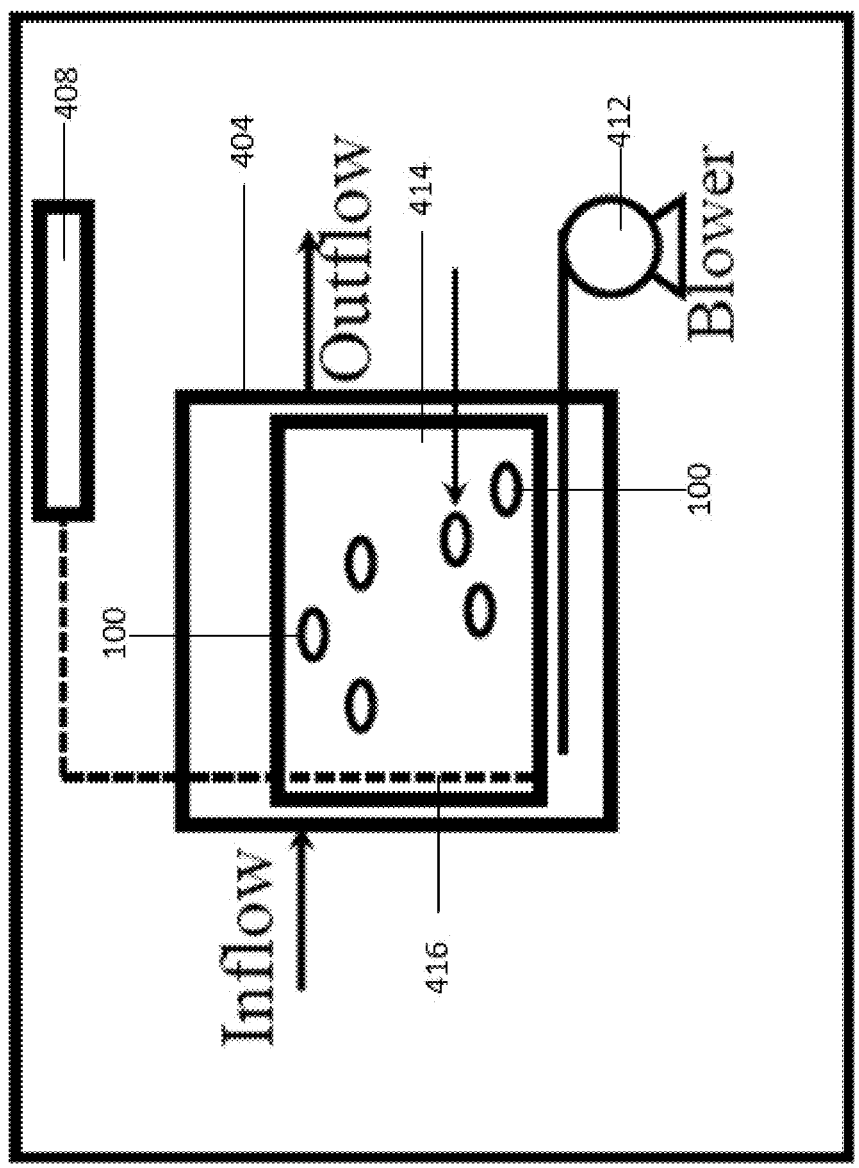
FIG. 4 is a cross-section view of the apparatus according to yet another embodiment of the present invention.

FIG. 4 is a cross-section view of yet another embodiment apparatus 400 for treating wastewater. Apparatus 400 is similar in construction and operation to apparatus 300, as detailed above, except where indicated. Apparatus 400 includes a body 404 defining a fluid flow path that extends from an inlet to an outlet. The inlet and outlet define a flow path of wastewater through the body 404. Body 404 includes a perforated cage or net 414 enclosing SBP capsules 100 and a blower or bubbler 412. Apparatus 400 further includes an external UV source 408 that is connected to body 404 using an optic fiber 416 or other light transporter. Optic fiber 416 is used for transmitting the UV radiation generated by the UV source 408 into the perforated cage 414. In one embodiment, the UV lamp or LED can be placed inside the perforated cage 414 near the SBP capsules 100.

EXAMPLES

The following examples are not meant to limit the scope of the claims in any way. The following examples are put forth so as to provide those of ordinary skill in the art with a complete disclosure and description of how to make and use the described invention, and are not intended to limit the scope of the invention, nor are they intended to represent that the experiments below are all or the only experiments performed. Unless indicated otherwise, parts are parts by weight, molecular weight is weight average molecular weight, temperature is in degrees Centigrade, and when temperature is not specifically mentioned the temperature is room temperature (approximately 25 degrees Celsius), and pressure is at or near atmospheric.

Example 1

SBP Particle Manufacture

Freeze-Dried Microorganism (Bacteria) Manufacture

A freeze-dry method to produce a dry bacteria/microorganism powder according to previously described protocols

[Leslie, S. B., et al., Appl Environ Microbiol (1995) 61(10): 3592-7; Sinskey, T. J. and G. J. Silverman, J Bacteriol (1970) 101(2): 429-37; Morgan, C. A., et at, J Microbiol Methods (2006) 66(2): 183-93; Costa, E., et al., J Appl Microbiol (2002) 92(5): 873-8] was used. The following steps were carried out:
1) Bacteria (*E. coli* TG1, *E. coli* TG1 pChv1, or *E. coli* DH5.alpha.) were grown overnight at 37° C., 200 rpm, 18 h, in 1 L growth medium comprising 0.5% yeast extract, 1% tryptone, 0.5% NaCl, and 5% sucrose (as a protecting freeze agent).
2) The culture was centrifuged (10 min, 7000 g, 4° C.).
3) The culture was suspended in 8 ml ice cold phosphate buffer solution (PBS, Sigma).
4) The suspended culture was centrifuged (10 min, 7000 g, 4° C.).
5) The culture was suspended in 8 ml ice cold PBS comprising 5% sucrose.
6) Steps 4-5 were repeated.
7) The culture was incubated at room temperature (22° C.) for 20 minutes, and was then divided into 1 ml doses for future viability counts (saving the precise volume).
8) The culture was incubated for 48-72 h at −80° C.
9) The culture was freeze-dried for 52 h (1 Pa, −45° C., 10 mm 171 g).
9) The dried culture was then stored at room temperature inside a dissector.

Inner Core Design and Manufacture

The inner cores were made of LA (Luria Agar-0.5% yeast extract, 1% tryptone, 0.5% NaCl and 0.185% agar) which were cast into 96 wells plates. After the polymerization of the LA, the inner cores were released from the plates onto petri dishes for drying in a biological hood for 72 hours. Next, the inner cores were sterilized using UV radiation within the biological hood for several hours.

Other Inner Particle Components

Glass beads (1 mm diameter) were added to the particles to increase the weight of the particle and to provide additional surface area for biofilm formation.

The Particle Construct

Gelatin capsules, size 000, were used to integrate all the inner components (microorganisms, inner core and glass beads) and to provide the foundation to build the outer membrane of the particle.

Constructing the Outer Membrane

Two types of polymers were used to construct the outer membrane, ethyl cellulose and cellulose acetate as follows:

Ethyl Cellulose (EC) Outer Membrane Coating

Ethyl cellulose polymer solution was prepared using a mix of two solvents, methanol and acetone, along with a plasticizer such as castor oil.

The protocol of the polymer solution:

Solution solvents (92%): 80% acetone and 20% methanol.

Suspended solids (8%): castor oil (12%) and ethyl cellulose (88%) (TAIAN RUITI CELLULOSE LTD., China).

The prepared solution was mixed with a stirrer for at least half an hour. Next, a spray was used to coat the gelatin capsules with the polymer. The particles were put on an upside down 96-well plate and sprayed 4-5 times on each side. The polymer solution volume was calculated according the required thickness of the particle (determined according to the required resistance for a cutting force for a given time). 13 ml or 15 ml of the polymer solution was used for coating of one particle. For ethyl cellulose, 6% and 8% suspended solids were used within the polymer solution and the stability of both formulations was tested.

Cellulose Acetate Outer Membrane Coating

The cellulose acetate polymer solution was prepared using a mix of two solvents, methanol and acetone, along with a plasticizer such as castor oil.

The protocol of the polymer solution:

Solution solvents (92%): 80% acetone and 20% methanol.

Suspended solids (8%): castor oil (12%) and cellulose acetate (88%) (EASTMAN, Switzerland).

The prepared solution was mixed with a stirrer for at least half an hour. Next, a spray was used to coat the gelatin capsule with the polymer. The particles were put on an upside down 96-well plate and sprayed 4-5 times on each side. Each particle was coated with 8 ml of the polymer solution.

Example 2

Contaminant Type Characterization

The contaminants optimal excitation wavelength may be determined prior to the treatment and according to environmental or medium conditions, such as bioreactor medium pH and the like. When the system and method of the present invention is configured to treat several types of contaminants simultaneously, a suitable polychromatic UV system may be defined.

Example 3 pH and pKa of Contaminant

Changes in molar absorption coefficient, due to pH modifications, are evident for most compounds and may provide a partial explanation for the compounds degradation rate changes and variations at different pH values. However, various compounds showed significant changes in their photodegradability, due to pH modification, with no associated changes in their molar absorption coefficient (e.g. CPZ). Therefore, varied mechanisms may be involved in the observed changes regarding the kinetics of the UV photodegradation of each compound by pH modification (e.g. changes in QY). Photolysis rates of several examined compounds (i.e. CBZ and ACR) are dependent on pH, however direct photolysis is not effective for their degradation due to the high UV doses above values of 6765 and 10474 mJ $cm^{-2}$ that are required for 90% removal of CBZ and ACR, respectively (at their optimal pH value). The pH modification can influence the 'electronic' (molecular/atomic) structure (e.g., extent or degree of double bond conjugation) of the target water contaminant, the absorbance, and hence the potential for photolytic degradation when irradiated at the relevant wavelength. Thus, there may be a relationship between the pH, molecule structure to its absorbance.

Example 4

Light Source

UV irradiation is a well-established practice for water disinfection of pathogens and oxidation of micro-pollutants. Polychromatic medium-pressure (MP) lamps require high drive voltage, produce a lot of heat resulting in high fouling and consequently need for frequent and expensive chemical and mechanical maintenance. Optionally, it is possible to use external UV light source and photons delivery into the water by using an optic wire/cable. The UV-light emitting diodes (LED) are considered a new UV source that can replace conventional mercury gas-filled lamps in water disinfection. UV LEDs emit light at different UV ranges (UVA/B/C). UV-LEDs are monochromatic (i.e. emit at a very narrow wavelength band), are selectable, thus emission spectrum can be tailored, require no warm up period, are flexible and have lower electricity consumption. In contrast to mercury lamps, LEDs are safe to dispose.

Example 5

Type of Encapsulated Microbe and Implementation Data

A. SBP capsules type adjustment: The SBP capsules are configured to provide sufficient amount of selective biomass in order to metabolize the target contaminants. Therefore, it is important to adjust microorganisms' culture (heterogenetic or homogenetic) to have the desired metabolic paths that enable using the contaminant as a Carbon source and/or as an energy source. It may be possible to implement several types of SBP capsules encasing different types of microorganisms population sets, in order to treat several contaminants in parallel or/and to design a multi-stages bio-chemical paths that can employ the contaminants as a Carbon source and/or as an energy source for each microorganism culture consumers.

B. Biomass quantity requirements (SBP dose administration): it may be important to determine the ratio between contaminant/s concentration and Oxidative Bio-Reactor (OBR) hydraulic retention time (the ratio OBR volume and daily inflow capacity). In addition, a protocol for periodically adding SBP capsules may be defined prior to the treatment. Biomass age (MCRT-mean cell residence time) and SBP membrane wear may be defined for the treatment process and medium conditions.

C. Biomass implementation site within the OBR system: SBP capsules implementation site may be considered prior to the system operation for treatment yield and efficacy elevation. The SBP capsules can either be implemented within the OBR inside one or more perforated cages, which allow us to control the biomass implementation site within the OBR or/and may be suspended to allow free movement inside the OBR. Each implementation technique might have a significant effluence on treatment yield and efficacy elevation.

Example 6

Pretreatment to OBR Process

In order to increase treatment yield and efficacy and in order to avoid some operational dysfunctions, pretreatment may be considered. Filtration, coagulation & flocculation process, oil/water separator and advance oxidative processes (ADP's) are few samples for possible pretreatment processes prior to the OBR treatment. Chemical oxidation is defined as electron transfer from an electron donor (reductant, with lower affinity to electrons) to an electron acceptor (oxidant, with higher affinity to electrons), resulting unstable highly reactive radicals which further react with reactants in the water until reaching a thermodynamically stable species. In water treatment applications, chemical oxidation is used to degrade organic contaminants in water through reaction mechanisms that result in a change in structure and chemical properties of the organic substance. Advanced. Oxidation Processes (AOP) involve generation of hydroxyl radicals, exploiting the high reactivity and unselectively of the intermediate hydroxyl radicals (OH·) to attack the organic molecules at accelerated rate constants vs. standard oxidation processes (kOH, organic substance, usually in order of 106-1011 M-1S-1). The hydroxyl radical (OH·) attack, in the presence of oxygen, initiates a complex cascade of oxidative reactions which leads to mineralization of the organic molecule. The following set of equations represents a typical reaction of the abstraction of a hydrogen atom to initiate a radical chain oxidation:

$$RH + OH \cdot \rightarrow H_2O + {}^\circ R \qquad (1)$$

$$2OH \cdot \rightarrow H_2O_2 \qquad (2)$$

$$^\circ R + H_2O_2 \rightarrow ROH + OH \cdot \qquad (3)$$

$$^\circ R + O_2 \rightarrow ROO \cdot \qquad (4)$$

$$ROO \cdot + RH \rightarrow ROOH + {}^\circ R \qquad (5)$$

The effectiveness of an AOP process is theoretically proportional to its capability to generate hydroxyl radicals, however elevated production of hydroxyl radicals may also result in lower reactivity due to their short living, recombination tendency, hence ineffective for the oxidation process. Photolytic dissociation of hydrogen peroxide by the UV radiation directly generates two hydroxyl radicals:

$$H_2O_2 \overset{hv}{\rightarrow} 2OH \cdot (\lambda \leq 300 \text{ nm}) \qquad (1)$$

Furthermore, an acid-base equilibrium between $HO_2^-$ and $H_2O_2$ may also adsorb the UV radiation to promote additional formation of hydroxyl radicals:

$$H_2O_2 \overset{hv}{\leftrightarrow} HO_2^- + H^+ \qquad (2)$$

$$HO_2^- \overset{hv}{\rightarrow} OH \cdot + O \cdot^+ (\lambda \leq 254 \text{ nm}) \qquad (3)$$

The oxidation of organics occurs by either the direct photolysis or the reaction with the hydroxyl radicals, both resulting in the destruction of the organic compounds. Accelerating the decomposition of hydrogen peroxide to produce as many hydroxyl radicals as possible may enhance the oxidation efficiency.

Example 7

Reactor Design (Hydraulic, Photon Exposure, SBP Capsules Location, etc.)

The OBR system is designed to include two major components: UV light source and SBP capsules encasing desired biomass. This treatment combination is the core technology of the OBR system. Possible system configurations: 1. The OBR system can act as single bioreactor for the treatment process or an additive treatment system. 2. The OBR can be designed and used prior or post major treatment process, or it can function as the major treatment system. 3. The OBR can treat a side stream in order to exclude certain contaminants in addition to non-selective organic matter. The OBR system may be designed and may operate according to the required system configuration and the adjustment requirements for selective contaminants removal and an existing infrastructure. The OBR can act in three possible operational modes: batch, semi-continuous and continuous mode.

Example 8

Biomass Viability Under Low Pressure (LP) UV Radiation

The efficacy of the SBP technology to provide a sustained biomass under UV irradiation was examined. Exposure of suspended and encapsulated bacteria (inside SBP capsules) to UV irradiation showed no change in the concentration of the suspended and encapsulated bacterial states as long as the UV lamp was turned off (0-100 minutes). Once the UV lamp turned on, the suspended bacteria concentration decreased rapidly (from $1.10 \times 10^7$ to $3.03 \times 10^3$ CFU/ml) while no change was observed in the SBP encapsulated culture. This proves that UV irradiation did not penetrate the microfiltration membrane of the SBP capsules as the inner media bacterial numbers remained equal with and without UV irradiation. These results demonstrate the resistance of encapsulated microorganisms to UV, and that the capsules provide a sufficient protective harrier to the inner bacterial capsule. These results demonstrate that SBP encapsulated bacteria can be active under long term treatment of UV irradiation (over 100 minutes of UV radiation exposure).

Example 9

Medium Pressure (MP) UV Radiation Effect on Bacterial Concentration within the SBP Particle In order to evaluate the effect of 10 minutes MP UV dose on the SBP internal medium bacterial concentration two study groups were used: 1. a test group which encased 5 SBP capsules that were exposed to 10 minutes of MP UV dose. 2. a control group that encased the same type of SBP capsules without the exposure to UV radiation, Samples of viable counts were administered after 0 h, 22 h, 36 h and 48 h. Viable counts from the inner medium of the SBP capsules revealed that after 10 minutes of exposure to MP UV radiation, the measured bacteria concentration was $5.5 \times 10^7$ CFU/ml, while within the control group the observed bacterial concentration was $4.6 \times 5 \times 10^7$ CFU/ml. These results emphasize that the SBP capsules can provide a good protective layer to the bacteria from 10 min MP UV radiation.

Example 10

The Establishment of 17α-ethynylestradiol (EE2) Analytical Method

This study was conducted in order to monitor EE2 concentration by using HPLC analysis. EE2 was chosen as a model molecule for CBR efficacy evaluation. Acetonitrile was acquired from BioLab, 17α-ethynylestradiol (EE2) was acquired from Sigma-Aldrich and the D.I. water was generated by Milipore directQ. The experiments samples (stored in 2 mL Eppendorf vials) were centrifuge for 10 minutes at 10,000 rpm. The clear upper adequate liquid was taken for analysis. Analysis was conducted by Agilent 1100 series HPLC coupled with a UV-DAD detector at 223 nm. Kinetex Evo, 100×3.0 mm, 2.6μ column at temperature of 40° C. was used. The mobile phase contained a mixture of water and acetonitrile (60:40% v/v) run by isocratic mode. The flow rate was at 0.4 mL/min and the injection volume was 60 μL. Stock standard solution were prepared by weighing ~10 mg of EE2 into 10 mL volumetric flask, dissolve in 5 mL Acetonitrile using sonic, and adding 5 mL of D.I. water.

Example 11

Medium Pressure UV Lamp to Find EE2 Extinction Coefficient

The breakdown of the treatment resistance molecule 17α-ethinylestradiol (EE2) was examined. EE2 is the main ingredient in oral contraceptive pills. The synthetic estrogen EE2 has been detected at nanogram per liter levels (ppt's) in both surface water and domestic wastewater effluents, which effect mainly aquatic environments even in the extremely low concentration, such as 0.1 ng/L. The EE2 hormone is considered the main cause for estrogenic activity in wastewater treatment effluents among the natural estrone (EE1), 17β-estradiol (EE2) and estriol (EE3). EE2 appears to degrade less than the natural hormones due to its stable chemical structure and therefore was chosen to simulate a treatment resistance molecule model. Photolysis was carried out using a 0.45 kW (200-300 nm) medium-pressure (MP) (Ace-Hanovia Lamp Cat. No. 7830 61, from Ace Glass Inc.) Hg vapor lamp housed in a quasi-collimated beam apparatus. A 100 mL sample with a starting concentration of 0.5 ppm (0.5 mg/L) EE2, 0.0235% Acetonitrile and 10 mM PBS pH=7.5 irradiated with gentle stirring in a 70×50 mm crystallization dish (33.2 cm² surface area, solution depth approximately 2.8 cm) open to the atmosphere. Samples of 0.5 mL were withdrawn for chromatography analysis, determination and quantification of EE2 residual. Exposure time of 10 minutes necessary to achieve UV influence 780 mJ/cm² was determined from the average irradiance between 200-300 nm. The average irradiance was calculated using the solution spectral absorbance, the spectral incident irradiance obtained from a calibrated spectro-radiometer (RPS900 wideband, international Light, Co., Newburyport, MA) placed in the same position as the center of the crystallization dish, the reflection at the sample surface and the measured petri-factor for the dish (Bolton & Linden2003). The average irradiance value for the MP lamp (integration between 200-300 nm) for 0.5 mg/L EE2 in 0.0235% Acetonitrile in 10 mM PBS at pH=7.5 was 1.30 mW/cm².

Figure 5:
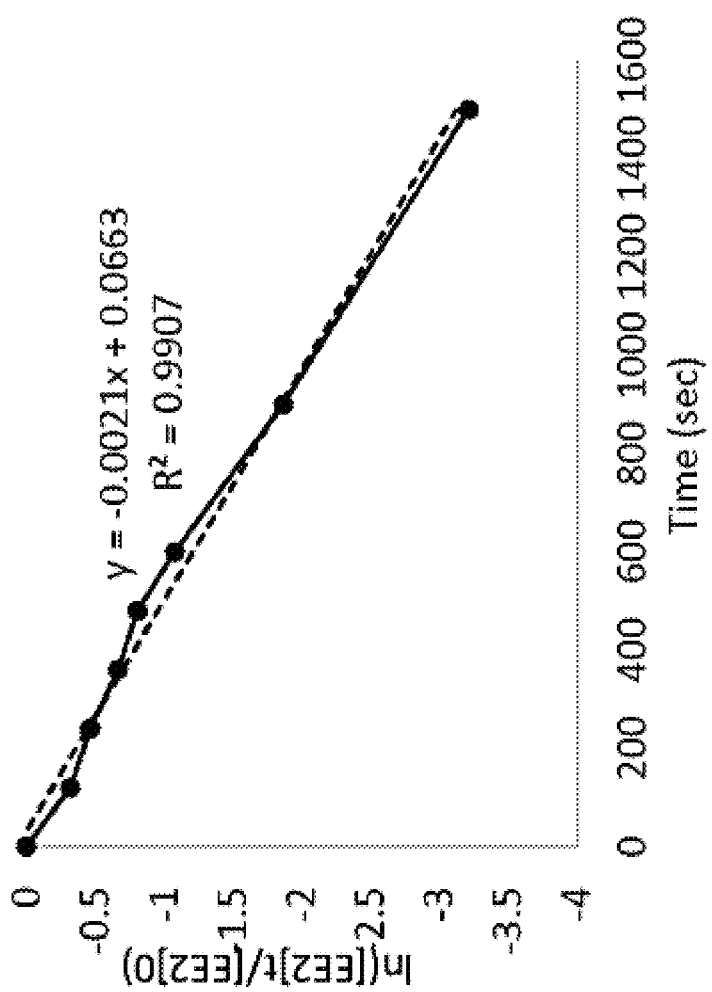
FIG. 5 is a representation of the photo degradation of EE2 (17α-ethinylestradiol) with medium-pressure (MP) lamp at pH of 7.5.
Figure 6:
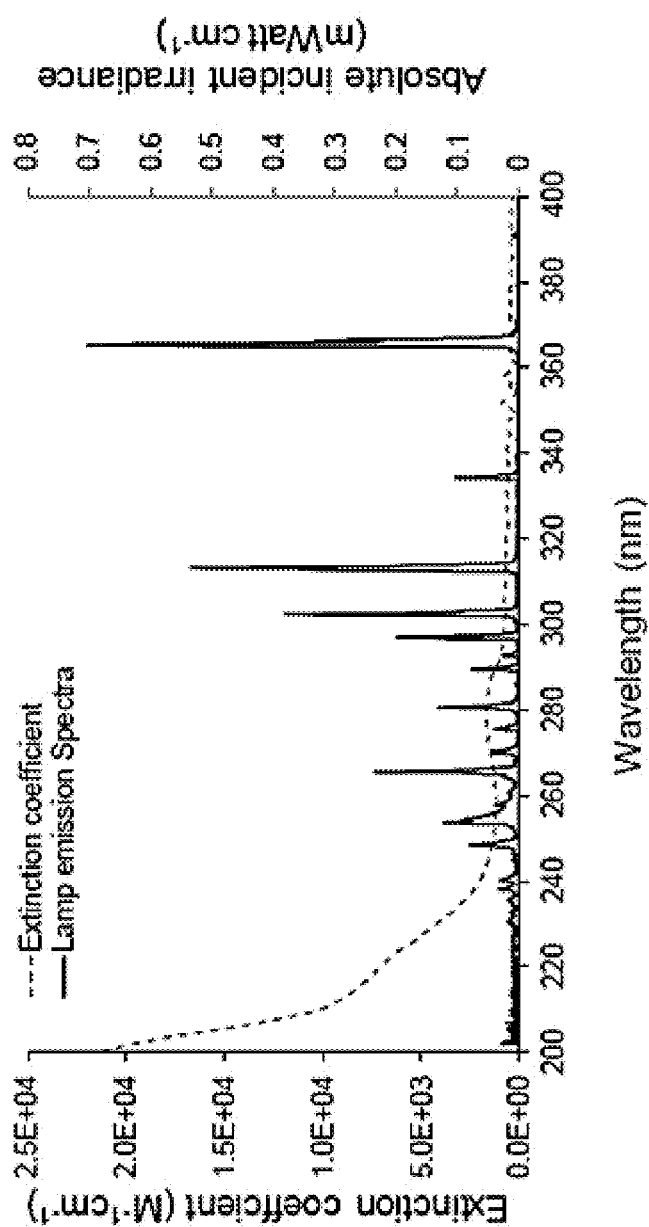
FIG. 6 is a representation of the extinction coefficient of 0.5 mg/L EE2 in 0.0235% Acetonitrile in 10 mM PBS at pH=7.5 and emission spectrum of the MP lamp.

Photo-degradation of 0.5 mg/L EE2 in aqueous solution by the polychromatic MP lamp as a function of time is illustrated in FIG. 5. In all cases, linear reaction kinetics occurs between $\ln([EE2]t/[EE2]0)$ and exposure time, where [EE2]0 is initial EE2 concentration and [EE2]t is EE2 concentration at time t. The data were fitted using a linear regression approach resulting in pseudo-first order reaction kinetics which reflects the difference in photo degradation between samples. The slope of the lines in FIG. 5 give the time-based rate constant, however, the fluence-based rate constant (cm²/mW) was also obtained and tabulated in FIG. 6.

Example 12

Figure 7:
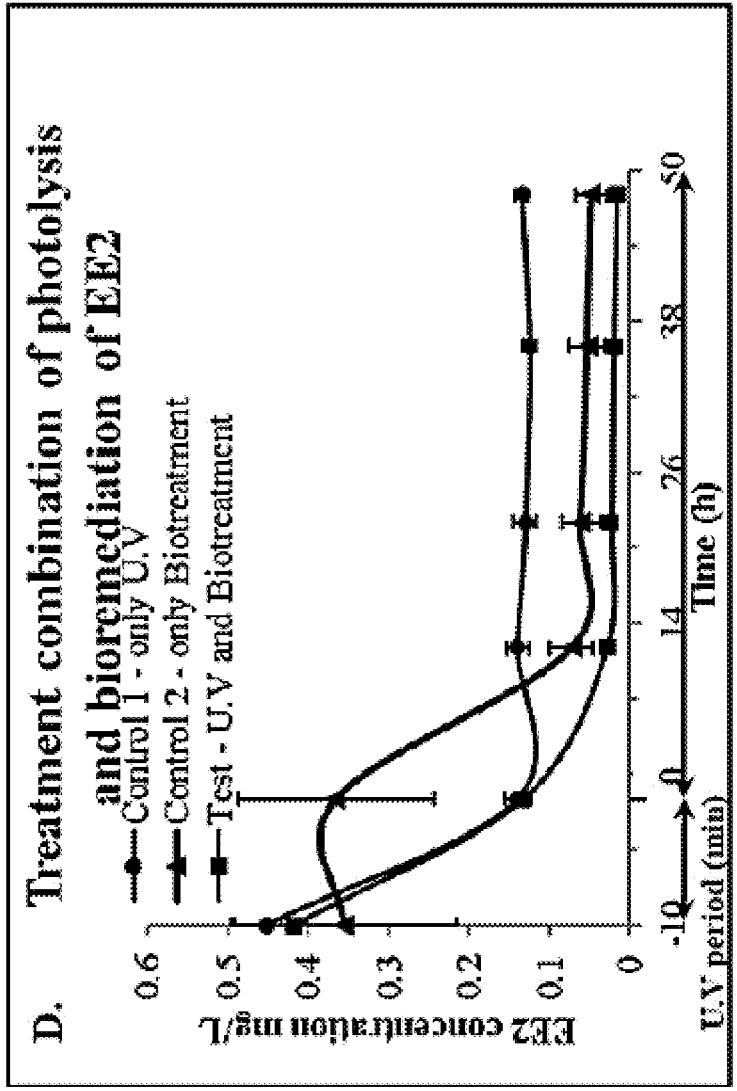
FIG. 7 is a representation of EE2 treatment combination of photolysis and bioremediation using $R.$ $zopfii$ SBP capsules, in PBS medium.

Dual Treatment Process: MP Photolysis (UV) and Bio-Treatment for EE2 (17α-Ethinylestradiol) Biodegradation A dual stage of photolysis treatment prior to the bioremediation stage was used in order to determine if a better EE2 biodegradation efficiency can be achieved. The experimental medium was 10 mM PBS encasing 5% LB. In the test system, samples were UV-irradiated for 10 min prior to the bio-treatment. In this trial, we used two types of control systems: control 1 encasing only EE2-UV-irradiated medium, and control 2 containing only EE2 bioremediation carried out by SBP encapsulated R. zopfii capsules which have well known capability to biodegrade EE2 molecules. Each control system represents a sole treatment potential of EE2 biodegradation. The test system presents a dual treatment for EE2 remediation; first we use UV radiation treatment for 10 minutes forward transferring the radiated medium into a flask containing the activated R. zopfii SBP capsules for the second treatment stage (bio-degradation treatment). FIG. 7 presents the EE2 concentration reduction over time and treatment. After 10 min of UV exposure (point −10 to 0), we observed a significant reduction in the EE2 concentration: 68% from the initial concentration. Following the UV irradiation stage and after 12 h of incubation of R. zopfii capsules, the EE2 concentration was further reduced by 27% (total reduction of 92.5%). Nonetheless, control 2 exhibited an EE2 reduction only by the biological process of almost 80% after 12 h of incubation. These results indicate that MP UV exposure might increase EE2 biocompatibility for the biodegradation process and the majority of EE2 molecules were degraded within 12 h of incubation time (93% from the initial EE2 concentration). EE2 UV exposure combined with bioremediation by a selective bacterial culture may present the most rapid biodegradation rate and efficacy over time (12 h), postulating a good possibility of a sustainable cost-effective tool against OMP's.

Example 13

Combined Treatment (Laboratory OBR Treatment Model): MP Photolysis (UV) Single Dose (10 Minutes of Operation) and Bio-Treatment for EE2 (17α-Ethinylestradiol) Biodegradation in One Chamber Combined photolysis with Rhedoccocus zopfii capsules treatment to decompose 0.5 mg/L EE2 in 0.0235% ACN in 10 mM PBS pH=7.5.

This study was conducted to verify the use of combined treatment (biological and physical treatment). In this case, UV and bio-treatment protected by the SBP capsules were evaluated to achieve a better treatment yield (efficacy and kinetic rate) for treatment resistance molecule model—EE2 (17α-ethinylestradiol).

Stage Number 1: Activation of 10 Rhedoccocus zopfii Capsules
1. SBP capsules were washed by 70% ethanol solution for 60 seconds (by dipping, using forceps). 10 capsules were implemented within 2 Erlenmeyers (250 mL sterile breathable Erlenmeyer comprising 5% LB in 1.0 mM PBS (100 mL)).
2. The SBP capsules were incubated (30° C., 150 rpm) for 5 days.
3. A day prior to the experiment, fresh LB was added to reach 5% LB Medium (2%) in PBS and final 0.5 ppm EE2-13.11.07.

Stage Number 2: The Experiment:
The experimental system includes a dual system (control & test).

The control systems: System 1 (Control 1)—Had the medium enriched with EE2 under a photolysis treatment (UV radiation), without the SBP capsules. System 2 (Control 2)—had only the biological system including the SBP capsules (5 capsules) without having the UV radiation phase (photolysis treatment). Control system 1 was aimed to evaluate the potential degradation efficacy of 10 min UV dose (Phase I), while control system 2 was aimed to evaluate the efficacy potential of the bio-treatment itself for 24 h. The test system (OBR process) with the 5 SBP capsules under 10 minutes of UV radiation (Phase I) and continued incubation and bio-degradation activity for 24 h after the photolysis treatment (Phase II).

Phase I—The Combined Treatment (OBR):
The procedure:
1. UV MP-0.5 mg/L EE2 (0.09% ACN) exp. was performed in duplicates, for capsules with and without 10 minutes MP irradiation*4.
2. All experiments were carried in solution containing: −0.5 mg/L EE2/−0.09% ACN in 10 mM PBS pH=7.5, using sterile 100 mL 70*40 beaker and a sterile magnet.
3. 100 mL beakers w/magnet (0.5 ppm EE2 in 10 mM PBS PH=7.5)*4 were prepared.
4. After MP, a cover of sterile petri dish cover to place beaker in hood (*4).
5. Withdraw (in hood) 1 mL (of 102 mL mixed sample)-0 photolysis*4.
6. 10 minutes irradiation beaker is to be covered with sterile petri dish placed in hood-withdraw 1 mL in hood.
7. Starting the process of radiation (PHOTO 0 till 0 HR) first with control samples (no UV) #1 and #2 and soon after the test samples.
8. Samples for analysis: Aliquots of 1000 ∞L for each UV-dose will be taken every, 10 minutes, 3 HR, 6 HR, 8 HR, 12 HR, 24 HR from initial volume of 102,000 μL In this phase, we conducted a dual treatment at the same time and place: Activated SBP biomass encases R. zopjii bacterial culture conducted a biodegradation treatment for EE2 under a single dose of UV radiation (10 minutes).

Samples time slides: Prior UV radiation (time 0) and after 10 minutes of UV radiation dose.

Phase II (Continuing the Bio-Treatment Along):
This phase was aimed to provide some information about the influence of a short term UV radiation (MP) treatment dose (single dose) on EE2 biodegradation for up to 24 h after the UV treatment (photolysis treatment). After the photolysis stage (phase I), all systems (Erlenmeyers) were incubated for 24 h in 30 degrees Celsius.

Study Outlines Design:

| | System 1 (Control 1) | System 2 (Control 2) | System 3 (Test-OBR) |
| --- | --- | --- | --- |
| Treatment | UV (photolysis) only | Bio-treatment only (5 SBP Capsules) | Combined treatment (5 SBP Capsules + 10 minutes of MP UV dose) |
| Repeats | Duplicate | Duplicate | Duplicate |
| Sampling time slides | 0, 10 min (prior and after UV treatment) 0, 3 h, 7 h, 11 h, 12 h, 24 h | 0, 2 h, 7 h, 11 h, 12 h, 24 h | 0, 10 min (prior and after UV treatment) 0, 3 h, 7 h, 11 h, 12 h, 24 h |

Figure 8:
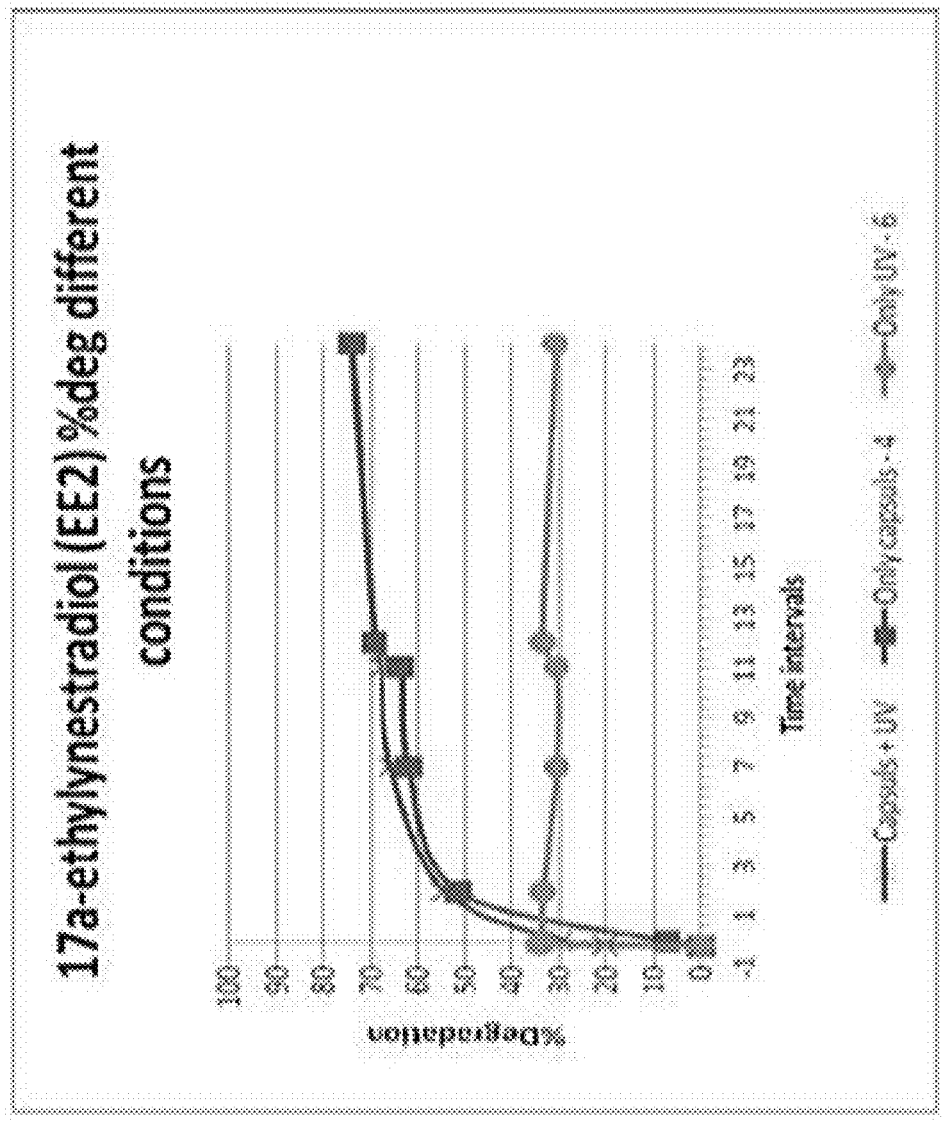
FIG. 8 is a representation of EE2 degradation (%) over time (h) by UV sole treatment, Bio-treatment and combined UV and Bio-treatment.

As seen in FIG. 8, the OBR treatment process although short (10 min) seemed to have a continuous influence up to 12 h (the line marked with X). Short term OBR process treatment presents a superior EE2 degradation efficacy over the bio-treatment (control 2) as a sole treatment. It appears that the short time (10 min) of UV energy investment has a positive effect on EE2 biodegradation using the SBP capsules. In addition, it was observed that the SBP capsules were providing a good protective confined environment for the selective biomass (*R. zopfii*) during the photolysis phase treatment. The SBP internal biomass was not affected by the photolysis treatment and moreover, the EE2 biodegradation rate and efficacy was improved during the first 12 h of incubation.

Example 14

Figure 9:
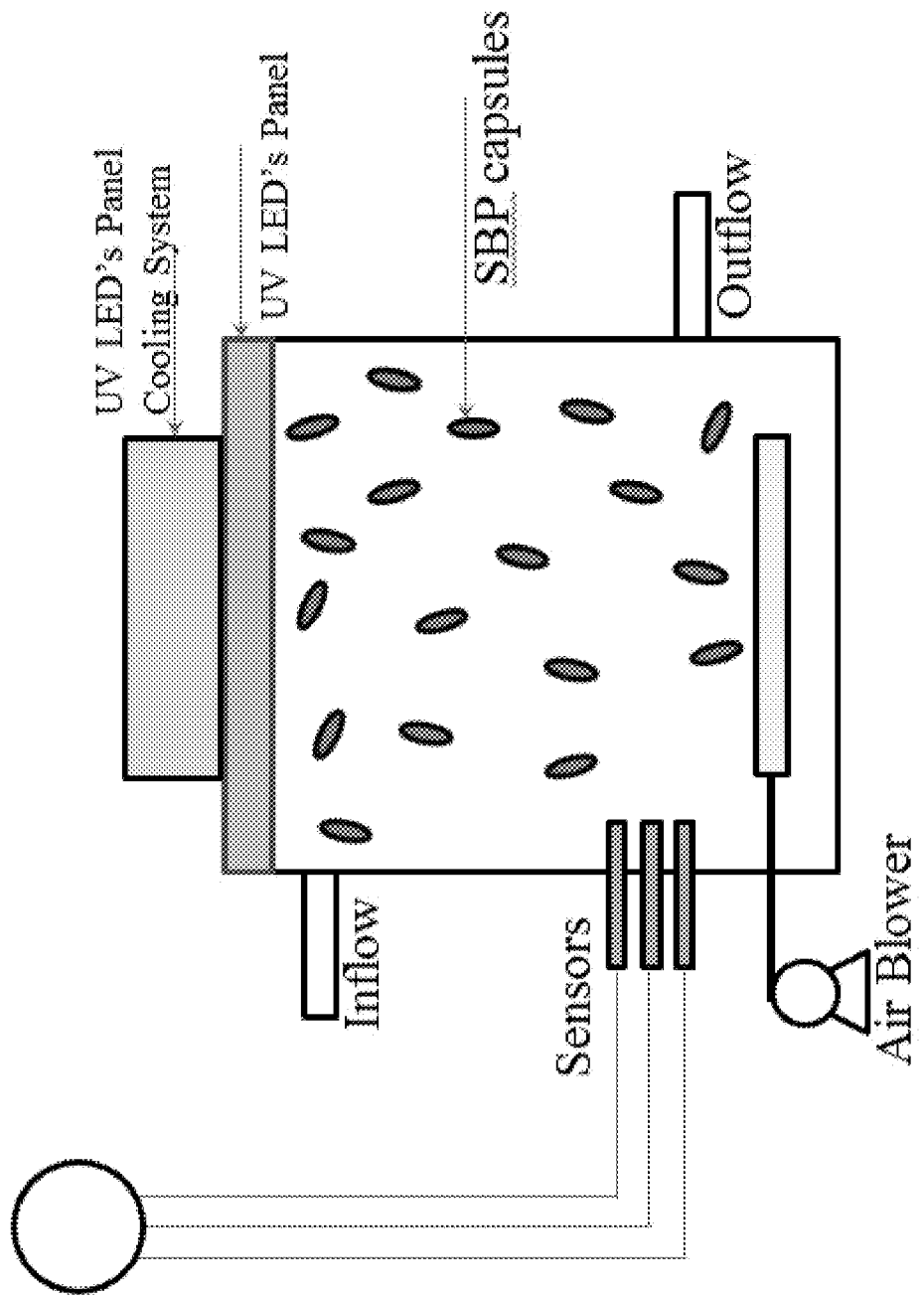
FIG. 9 is an illustration of a field treatment system prototype presenting EE2 treatment as a pharmaceuticals molecule model; and, FIG. 10 is a representation of EE2 degradation (%) over time (h) by the system prototype of FIG. 10.
Figure 10:
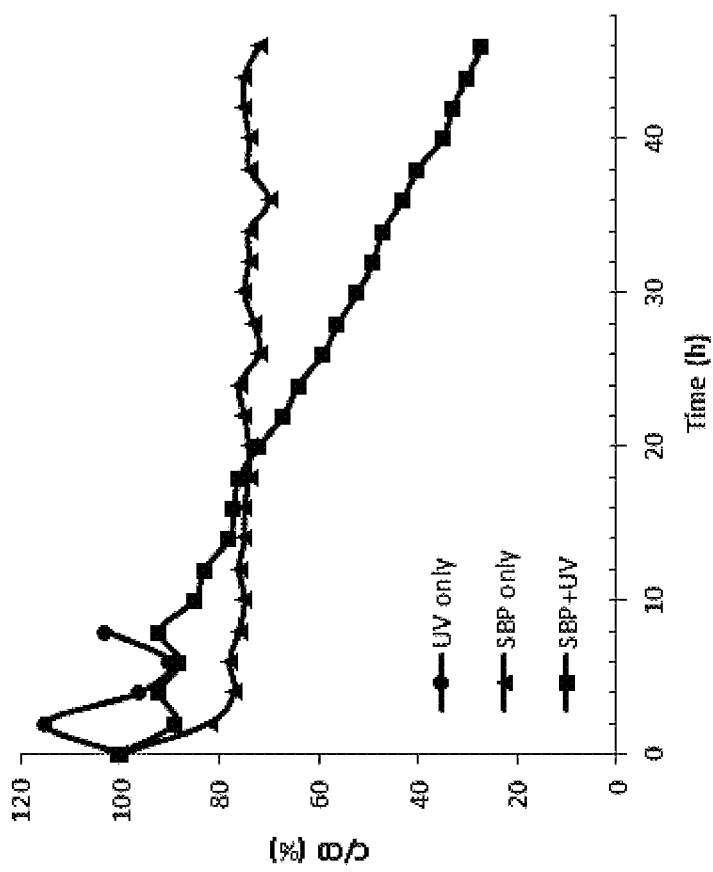

Field Configuration of OBR Treatment Model Prototype: LED Photolysis (UV) and Bio-Treatment (SBP) for EE2 (17α-ethinylestradiol) Biodegradation in a Single Chamber/Reactor 1. System description: 200 L (net) volume bioreactor made of stainless steel, encasing the following major components: A. UV LED panel B. A cooling system C. A diffuser attached to a blower D. Sensors electrodes: pH, D.O, and temperature. E. SBP Capsules encasing a selective bacterial culture.
UV matrix panel: The UV led panel matrix encases the following light wavelength (products of TAOYUAN ELECTRON (HK) LIMITED): 265 nm (Optical power-60 mW), 275-285 nm (Optical power-100 mW), 310 nm (Optical power-60 mW), 365 nm (Optical power-12000 mW), and 395 nm (Optical power-23000 mnW). Each wavelength is encasing 20 LED's. An overall of 100 UV LED's produce monochromatic or polychromatic UV light by choice. The UV panel is attached to the upper lead of the OBR. A cooling system is located above the UV light panel. The UV light panel is near the water surface of the bioreactor.
2. System characterization: FIG. 9 presents a treatment system prototype presenting EE2 treatment as a pharmaceuticals molecule model. This OBR prototype system can be operating in three hydraulic treatment options: 1. Batch treatment 2. Semi-continuous treatment and 3. Continuous treatment. A batch system mode was chosen in order to evaluate the EE2 concentration reduction over time by three tests procedures: 1. The use of UV light treatment only (polychromatic) The entire led panel was activated for several hours (UV treatment only). 2. The use of biological treatment only (200 SBP capsules encasing *R. zopfii* bacterial culture)—operated—for 48 h (Biological treatment only) and 3. Combined treatment of UV light and Biological treatment (200 SBP capsules encasing *R. zopfii* bacterial culture) operated together for 48 h. UV light treatment (all panel LED's) was activated constantly for 48 h. An automatic sampler system was used. Samples were analyzed by using the HPLC method as described in Example 10. The reactor medium was encasing a phosphate buffer and a nitrogen source ($NO_3$). The sole carbon source was EE2 dissolved in Acetonitrile (50 ml). SBP capsules encasing the bacterial culture *R. zopfii* were active a week before in saline and EE2 (as a carbon source). The activated. SBP capsules were washed and then added into the OBR prior to the tests.
3. Results (FIG. 10): A. UV sole treatment: The UV panel was activated for 8 hours (the OBR system did not have SBP capsules). There was no observed effect on EE2 concentration over time, B. Biological treatment as a sole treatment: 200 activated SBP capsules were added to the OBR system which is an equivalent to approximate 400 ml ($10^8$ CFU/ml) of suspended *R. zopfii* culture. During the first 4 h of incubation EE2 reduction was up to 23% and remained almost without a change up to 48 h of incubation (77% remaining from the initial EE2 concentration). C. Combined treatment of 48 h UV light and biological treatment (200 activated SBP capsules): After 8 h of incubation a steady reduction in EE2 concentration was observed. After 48 h of combined treatment, the remaining EE2 concentration ($C/C_o$) was 27% of the initial EE2 concentration. The combined treatment was the most effective treatment in comparison to each sole treatment (UV and biological) and may indicate a synergetic effect between the UV and biological treatment techniques. Viable counts of the bacterial culture within the SBP capsules after 3 weeks of treatment within the OBR indicated an internal concentration of $3.6*10^7$ CFU/ml.

While the invention has been described with respect to a limited number of embodiments, it will be appreciated that many variations, modifications and other applications of the invention may be made. Therefore, the claimed invention as recited in the claims that follow is not limited to the embodiments described herein.

The invention claimed is:
1. A method for treating liquids including contaminant molecules dispersed therein, the method comprising:
providing at least one capsule into a volume of a liquid including contaminant molecules dispersed therein to obtain a mixture consisting of said liquid and said at least one capsule, wherein said contaminant molecules comprise biodegradable molecules and non-biodegradable molecules; the at least one capsule is configured for treating biodegradable molecules; and
exposing the mixture to ultraviolet (UV) light for at least a time period sufficient for treating non-biodegradable molecules;
thereby treating the liquid; and
wherein each capsule comprises at least one inner core including a solid matrix of nutrients for microorganism growth and a population of microorganisms; and further comprises an outer porous membrane surrounding said inner core.
2. The method of claim 1, wherein the treating includes digesting the biodegradable molecules by the at least one capsule.
3. The method of claim 2, wherein the digesting the biodegradable molecules results in one or more of: Carbon Dioxide, secondary metabolites and, cell proliferations.
4. The method of claim 1, wherein the treating non-biodegradable molecules comprises converting the non-biodegradable molecules into biodegradable molecules, at least partially eliminating said non-biodegradable molecules from said liquid, or both.
5. The method of claim 1, wherein the treating the biodegradable molecules with the at least one capsule occurs while the mixture is exposed to the UV light for at least 24 h.
6. The method of claim 1, wherein the treating the biodegradable molecules with the at least one capsule occurs simultaneously with the mixture being exposed to the UV light for at least 10 min.
7. The method of claim 1, wherein the at least one capsule includes a plurality of capsules.
8. The method of claim 1, wherein the contaminant molecules are at least one of: treatment resistant molecules, and semi-resistant molecules.

9. The method of claim 1, wherein the treating the biodegradable molecules includes facilitating contact between each capsule and the biodegradable molecules.

10. The method of claim 9, wherein the facilitating contact includes at least one of stirring the mixture or creating turbulence in the mixture.

* * * * *